US011666282B2

(12) United States Patent
Shute et al.

(10) Patent No.: US 11,666,282 B2
(45) Date of Patent: Jun. 6, 2023

(54) DETECTING IMPLANTABLE MEDICAL DEVICE ORIENTATION CHANGE

(71) Applicant: Cardiac Pacemakers, Inc., St Paul, MN (US)

(72) Inventors: Jonathan Bennett Shute, Minnetonka, MN (US); John D. Hatlestad, Maplewood, MN (US); Scott R. Vanderlinde, Plymouth, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 348 days.

(21) Appl. No.: 16/894,943

(22) Filed: Jun. 8, 2020

(65) Prior Publication Data

US 2020/0383638 A1 Dec. 10, 2020

Related U.S. Application Data

(60) Provisional application No. 62/858,696, filed on Jun. 7, 2019.

(51) Int. Cl.
*A61B 5/00* (2006.01)
*A61N 1/365* (2006.01)
*A61B 5/06* (2006.01)

(52) U.S. Cl.
CPC .............. *A61B 5/686* (2013.01); *A61B 5/067* (2013.01); *A61B 5/6869* (2013.01); *A61B 5/721* (2013.01);
(Continued)

(58) Field of Classification Search
CPC .... A61B 2560/0223; A61B 2560/0242; A61B 2562/0219; A61B 5/0031; A61B 5/0205; A61B 5/021; A61B 5/024; A61B 5/067; A61B 5/0809; A61B 5/1112; A61B 5/1116; A61B 5/1118; A61B 5/14542; A61B 5/165; A61B 5/4815; A61B 5/686; A61B 5/6869; A61B 5/721; A61B 5/7239;
(Continued)

(56) References Cited

U.S. PATENT DOCUMENTS

2010/0249629 A1* 9/2010 Schmidt .................. A61B 7/04
600/528
2011/0172562 A1* 7/2011 Sahasrabudhe ........ A61B 5/742
600/587

(Continued)

OTHER PUBLICATIONS

International Search Report and Written Opinion received for PCT Patent Application No. PCT/US2020/036556, dated Sep. 7, 2020, 14 pages.

*Primary Examiner* — Yi-Shan Yang
*Assistant Examiner* — Alexei Bykhovski
(74) *Attorney, Agent, or Firm* — Faegre Drinker Biddle & Reath LLP

(57) ABSTRACT

Embodiments of the present disclosure relate to detecting implantable medical device orientation changes. In an exemplary embodiment, a medical device having a processor, comprises an acceleration sensor and memory. The acceleration sensor is configured to generate acceleration data that comprises a plurality of acceleration measurements. The memory comprises instructions that when executed by the processor, cause the processor to: obtain the acceleration data from the acceleration sensor; and determine, based on the acceleration data, that the medical device has flipped.

16 Claims, 5 Drawing Sheets

(52) U.S. Cl.
CPC ............ *A61B 5/725* (2013.01); *A61B 5/7239* (2013.01); *A61B 5/74* (2013.01); *A61N 1/36535* (2013.01); *A61N 1/36542* (2013.01); *A61B 2560/0223* (2013.01); *A61B 2562/0219* (2013.01)

(58) Field of Classification Search
CPC ......... A61B 5/725; A61B 5/74; A61B 5/6847; A61B 5/065; A61B 5/283; A61B 5/318; A61B 5/4806; A61N 1/36535; A61N 1/36542
See application file for complete search history.

(56) References Cited

U.S. PATENT DOCUMENTS

| | | | |
|---|---|---|---|
| 2013/0211205 A1* | 8/2013 | Havel | A61N 1/37282 600/301 |
| 2015/0286285 A1* | 10/2015 | Pantelopoulos | G06F 3/048 345/156 |
| 2016/0262685 A1* | 9/2016 | Wagner | A61B 5/1123 |
| 2018/0028808 A1* | 2/2018 | Ferree | A61B 5/4815 |
| 2018/0168449 A1* | 6/2018 | Kraetschmer | A61B 5/721 |
| 2019/0038938 A1* | 2/2019 | Nagasaka | B62J 45/42 |

* cited by examiner

DETECTING IMPLANTABLE MEDICAL DEVICE ORIENTATION CHANGE

CROSS REFERENCE TO RELATED APPLICATION

This application claims priority to Provisional Application No. 62/858,696, filed Jun. 7, 2019, which is herein incorporated by reference in its entirety.

TECHNICAL FIELD

Embodiments of the present disclosure relate to medical devices and systems for sensing physiological parameters. More specifically, embodiments of the disclosure relate to determining whether an orientation of a medical device has changed.

BACKGROUND

Implantable medical devices (IMDs) may be configured to sense physiological parameters and/or provide therapy. The overall usable volume enclosed within a housing of an IMD may be adjusted based on considerations of patient comfort and performance. Examples of IMDs include implantable cardiac monitors (ICMs), implantable loop recorders (ILRs), and the like, which can be configured to be subcutaneously implanted in a patient for monitoring one or more physiological parameters such as, e.g., physiological parameters associated with the heart and/or the lungs.

To facilitate a more comfortable and efficient experience, these devices may be designed to keep the overall volume of the device as small as possible. Each year, the devices become smaller and include sensors with more and more capabilities. In many cases, the orientation of the sensor relative to the body is an important input for many of the sensors and algorithms. Some of these devices have a relatively high probability of rotation in the body due to their geometry.

SUMMARY

Embodiments for detecting implantable medical device orientation changes include, but are not limited to, the following exemplary embodiments.

In an Example 1, a medical device having a processor, comprising: an acceleration sensor configured to generate acceleration data, the acceleration data comprising a plurality of acceleration measurements; and a memory having embodied thereon computer-executable instructions that are configured to, when executed by the processor, cause the processor to: obtain the acceleration data from the acceleration sensor; and determine, based on the acceleration data, that the medical device has flipped.

In an Example 2, the medical device of Example 1, wherein the instructions are configured to cause the processor to determine that the medical device has flipped by causing the processor to: generate a slope of the acceleration data, the slope comprising axis values for at least two axes against time; apply a moving mean filter across the data to generate a first smoothed set of axis data corresponding to a first axis and a second smoothed set of axis data corresponding to a second axis; identify an intersection between the first smoothed set of axis data and the second smoothed set of axis data; and determine, based on the identified intersection, that the medical device has flipped.

In an Example 3, the medical device of Example 1, wherein the instructions are configured to cause the processor to determine that the medical device has flipped by causing the processor to: generate a slope of the acceleration data, the slope comprising axis values for at least one axis against time; apply a moving mean filter across the data to generate a first smoothed set of axis data corresponding to a first axis of the at least one axis; identify a first sign change associated with the first smoothed set of axis data; and determine, based on the identified first sign change, that the medical device has flipped.

In an Example 4, the medical device of Example 3, wherein the instructions are further configured to cause the processor to apply the moving mean filter across the data to generate a second smoothed set of axis data corresponding to a second axis; identify a second sign change associated with the second smoothed set of axis data; and determine, based on the identified first and second sign changes, that the medical device has flipped.

In an Example 5, the medical device of any of Examples 1-4, wherein the instructions are further configured to cause the processor to apply, in response to determining that the medical device has flipped, a correction to an output of a monitoring process.

In an Example 6, the medical device of Example 5, wherein the monitoring process comprises at least one of a posture algorithm, a heart sounds algorithm, and an ICM impedance sensing process.

In an Example 7, the medical device of either of Examples 5 or 6, wherein the instructions are configured to cause the processor to apply the correction to the output of the monitoring process by recalibrating the monitoring process to account for a flipped orientation of the medical device.

In an Example 8, the medical device of any of Examples 1-7, wherein the instructions are further configured to cause the processor to generate, in response to determining that the medical device has flipped, a notification.

In an Example 9, the medical device of Example 8, wherein the notification comprises one or more recommendations for responding to the flipped medical device.

In an Example 10, the medical device of any of Examples 1-9, wherein the instructions are configured to cause the processor to determine that the medical device has flipped by causing the processor to: apply a trigonometric function to the acceleration data and identify a flip based on a resultant of the trigonometric function being applied to the acceleration data.

In an Example 11, a processor-implemented method, performed by a processor of a medical device, the method comprising: obtaining acceleration data from an acceleration sensor; and determining, based on the acceleration data, that the medical device has flipped.

In an Example 12, the method of Example 11, wherein determining that the medical device has flipped comprises: generating a slope of the acceleration data, the slope comprising axis values for at least two axes against time; applying a moving mean filter across the data to generate a first smoothed set of axis data corresponding to a first axis and a second smoothed set of axis data corresponding to a second axis; identifying an intersection between the first smoothed set of axis data and the second smoothed set of axis data; and determining, based on the identified intersection, that the medical device has flipped.

In an Example 13, the method of Example 11, wherein determining that the medical device has flipped comprises: generating a slope of the acceleration data, the slope comprising axis values for at least one axis against time; applying a moving mean filter across the data to generate a first smoothed set of axis data corresponding to a first axis of the at least one axis; identifying a first sign change associated with the first smoothed set of axis data; and determining, based on the identified first change, that the medical device has flipped.

In an Example 14, the method of Example 13, further comprising: applying the moving mean filter across the data to generate a second smoothed set of axis data corresponding to a second axis; identifying a second sign change associated with the second smoothed set of axis data; and determining, based on the identified first and second sign changes, that the medical device has flipped.

In an Example 15, the method of any of Examples 11-14, further comprising applying, in response to determining that the medical device has flipped, a correction to an output of a monitoring process.

In an Example 16, a medical device having a processor, comprising: an acceleration sensor configured to generate acceleration data, the acceleration data comprising a plurality of acceleration measurements; and a memory having embodied thereon computer-executable instructions that are configured to, when executed by the processor, cause the processor to: obtain the acceleration data from the acceleration sensor; and determine, based on the acceleration data, that the medical device has flipped.

In an Example 17, the medical device of Example 16, wherein the instructions are configured to cause the processor to determine that the medical device has flipped by causing the processor to: generate a slope of the acceleration data, the slope comprising axis values for at least two axes against time; apply a moving mean filter across the data to generate a first smoothed set of axis data corresponding to a first axis and a second smoothed set of axis data corresponding to a second axis; identify an intersection between the first smoothed set of axis data and the second smoothed set of axis data; and determine, based on the identified intersection, that the medical device has flipped.

In an Example 18, the medical device of Example 16, wherein the instructions are configured to cause the processor to determine that the medical device has flipped by causing the processor to: generate a slope of the acceleration data, the slope comprising axis values for at least one axis against time; apply a moving mean filter across the data to generate a first smoothed set of axis data corresponding to a first axis of the at least one axis; identify a first sign change associated with the first smoothed set of axis data; and determine, based on the identified first sign change, that the medical device has flipped.

In an Example 19, the medical device of Example 18, wherein the instructions are further configured to cause the processor to apply a moving mean filter across the data to generate a second smoothed set of axis data corresponding to a second axis; identify a second sign change associated with the second smoothed set of axis data; and determine, based on the identified first and second sign changes, that the medical device has flipped.

In an Example 20, the medical device of Example 16, wherein the instructions are further configured to cause the processor to apply, in response to determining that the medical device has flipped, a correction to an output of a monitoring process.

In an Example 21, the medical device of Example 20, wherein the monitoring process comprises at least one of a posture algorithm, a heart sounds algorithm, and an ICM impedance sensing process.

In an Example 22, the medical device of Example 20, wherein the instructions are configured to cause the processor to apply the correction to the output of the monitoring process by recalibrating the monitoring process to account for a flipped orientation of the medical device.

In an Example 23, the medical device of any of Examples 20, wherein the instructions are further configured to cause the processor to generate, in response to determining that the medical device has flipped, a notification.

In an Example 24, the medical device of Example 23, wherein the notification comprises one or more recommendations for responding to the flipped medical device.

In an Example 25, the medical device of Example 16, wherein the instructions are configured to cause the processor to determine that the medical device has flipped by causing the processor to: apply a trigonometric function to the acceleration data and identify a flip based on a resultant of the trigonometric function being applied to the acceleration data.

In an Example 26, a processor-implemented method, performed by a processor of a medical device, the method comprising: obtaining acceleration data from an acceleration sensor; and determining, based on the acceleration data, that the medical device has flipped.

In an Example 27, the method of Example 26, wherein determining that the medical device has flipped comprises: generating a slope of the acceleration data, the slope comprising axis values for at least two axes against time; applying a moving mean filter across the data to generate a first smoothed set of axis data corresponding to a first axis and a second smoothed set of axis data corresponding to a second axis; identifying an intersection between the first smoothed set of axis data and the second smoothed set of axis data; and determining, based on the identified intersection, that the medical device has flipped.

In an Example 28, the method of Example 26, wherein determining that the medical device has flipped comprises: generating a slope of the acceleration data, the slope comprising axis values for at least one axis against time; applying a moving mean filter across the data to generate a first smoothed set of axis data corresponding to a first axis of the at least one axis; identifying a first sign change associated with the first smoothed set of axis data; and determining, based on the identified first change, that the medical device has flipped.

In an Example 29, the method of Example 28, further comprising: applying the moving mean filter across the data to generate a second smoothed set of axis data corresponding to a second axis; identifying a second sign change associated with the second smoothed set of axis data; and determining, based on the identified first and second sign changes, that the medical device has flipped.

In an Example 30, the method of Example 26, further comprising applying, in response to determining that the medical device has flipped, a correction to an output of a monitoring process.

In an Example 31, the method of Example 30, wherein the monitoring process comprises at least one of a posture algorithm, a heart sounds algorithm, and an ICM impedance sensing process.

In an Example 32, one or more computer-readable media having computer-executable instructions embodied thereon, the instructions configured to be executed by a processor of a medical device, wherein the instructions are configured to cause the processor to: obtain acceleration data from an acceleration sensor; and determine, based on the acceleration data, that the medical device has flipped.

In an Example 33, the media of Example 32, wherein the instructions are configured to cause the processor to determine that the medical device has flipped by causing the processor to: generate a slope of the acceleration data, the slope comprising axis values for at least two axes against time; apply a moving mean filter across the data to generate a first smoothed set of axis data corresponding to a first axis and a second smoothed set of axis data corresponding to a second axis; identify an intersection between the first smoothed set of axis data and the second smoothed set of axis data; and determine, based on the identified intersection, that the medical device has flipped.

In an Example 34, the media of Example 32, wherein the instructions are configured to cause the processor to determine that the medical device has flipped by causing the processor to: generate a slope of the acceleration data, the slope comprising axis values for at least one axis against time; apply a moving mean filter across the data to generate a first smoothed set of axis data corresponding to a first axis of the at least one axis; identify a first sign change associated with the first smoothed set of axis data; and determine, based on the identified first sign change, that the medical device has flipped.

In an Example 35, the media of Example 32, wherein the instructions are further configured to cause the processor to apply, in response to determining that the medical device has flipped, a correction to an output of a monitoring process.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
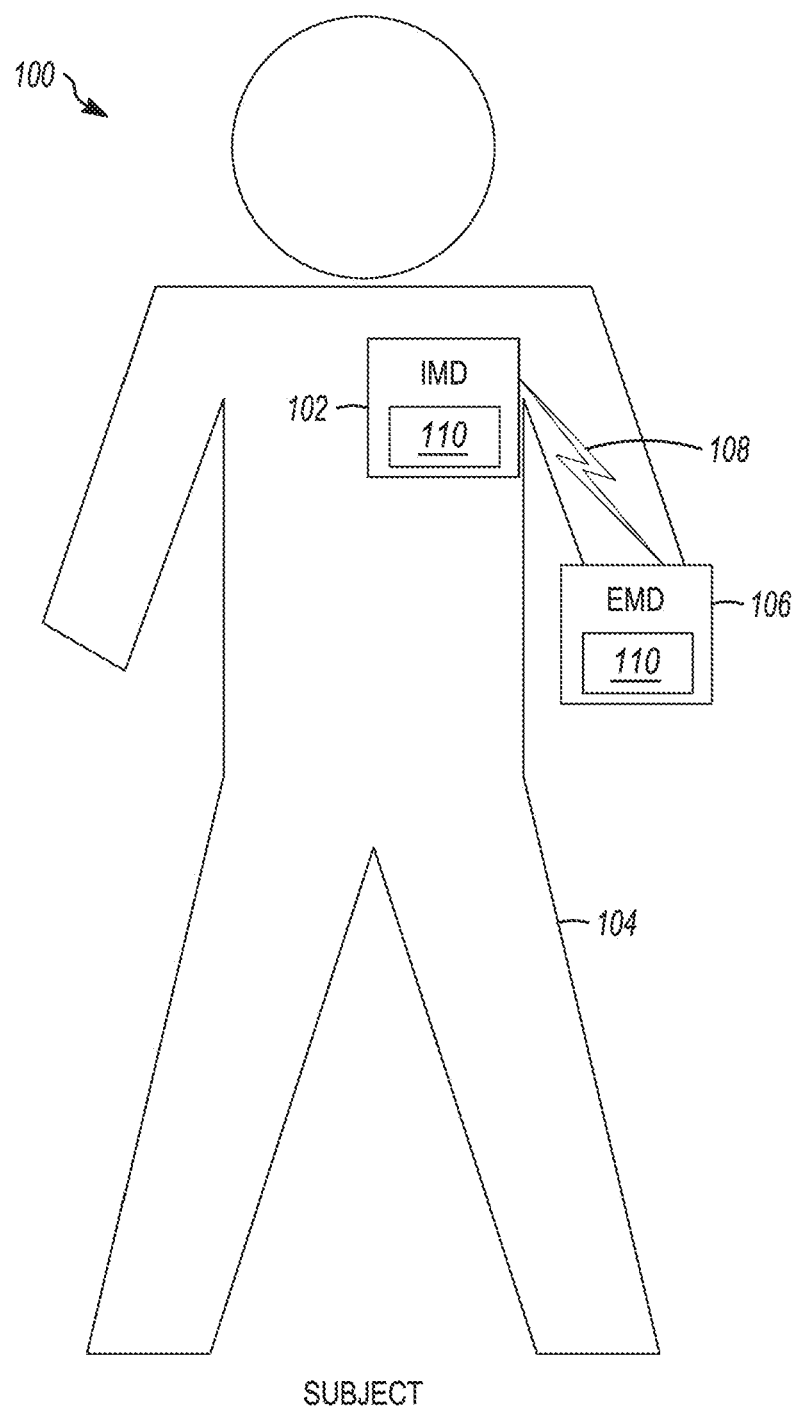
FIG. 1 is a schematic illustration depicting an illustrative medical system, in accordance with embodiments of the disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Embodiments of the disclosure include an implantable medical device (IMD) that includes a processor configured to determine a change in orientation of the IMD. That is, for example, in embodiments, the processor of the IMD may be configured to obtain acceleration data (e.g., posture data) and to process that data to determine whether the IMD has flipped. According to embodiments, an IMD has flipped when its orientation with respect to at least one axis has changed by approximately 180 degrees.

FIG. 1 shows an illustrative medical system 100, in accordance with embodiments of the disclosure. As shown in FIG. 1, the medical system 100 includes an IMD 102 configured to be implanted within the body of a subject 104, and an external monitoring device (EMD) 106, which is communicatively coupled to the IMD 102 via a communication link 108. In the illustrated embodiments, the medical system 100 is operatively coupled to the subject 104, and the IMD 102 and the EMD 106 are configured to communicate with one another over the communication link 108. The subject 104 may be a human, a dog, a pig, and/or any other animal having physiological parameters that can be recorded. For example, in embodiments, the subject 104 may be a human patient.

In embodiments, the communication link 108 may be, or include, a wireless communication link such as, for example, a short-range radio link, such as Bluetooth, IEEE 802.11, a proprietary wireless protocol, and/or the like. In embodiments, for example, the communication link 108 may utilize Bluetooth Low Energy radio (Bluetooth 4.1), or a similar protocol, and may utilize an operating frequency in the range of 2.40 to 2.48 GHz. The term "communication link" may refer to an ability to communicate some type of information in at least one direction between at least two devices, and should not be understood to be limited to a direct, persistent, or otherwise limited communication channel. That is, according to embodiments, the communication link 108 may be a persistent communication link, an intermittent communication link, an ad-hoc communication link, and/or the like. The communication link 108 may refer to direct communications between the IMD 102 and the EMD 106, and/or indirect communications that travel between the IMD 102 and the EMD 106 via at least one other device (e.g., a repeater, router, hub, and/or the like). The communication link 108 may facilitate uni-directional and/or bi-directional communication between the IMD 102 and the EMD 106. Data and/or control signals may be transmitted between the IMD 102 and the EMD 106 to coordinate the functions of the IMD 102 and/or the EMD 106. In embodiments, patient data may be downloaded from one or more of the IMD 102 and the EMD 106 periodically or on command. The physician and/or the patient may communicate with the IMD 102 and the EMD 106, for example, to acquire patient data or to initiate, terminate and/or modify recording and/or therapy.

In embodiments, the IMD 102 and/or the EMD 106 may provide one or more of the following functions with respect to a patient: sensing, data analysis, and therapy. For example, in embodiments, the IMD 102 and/or the EMD 106 may be used to measure any number of a variety of physiological, device, subjective, and/or environmental parameters associated with the subject 104, using electrical, mechanical, and/or chemical means. The IMD 102 and/or the EMD 106 may be configured to automatically gather data, gather data upon request (e.g., input provided by the subject, a clinician, another device, and/or the like), and/or any number of various combinations and/or modifications thereof. The IMD 102 and/or EMD 106 may be configured to store data related to the physiological, device, environmental, and/or subjective parameters and/or transmit the data to any number of other devices in the system 100. In embodiments, the IMD 102 and/or the EMD 106 may be configured to analyze data and/or act upon the analyzed data. For example, the IMD 102 and/or EMD 106 may be configured to modify therapy, perform additional monitoring, and/or provide alarm indications based on the analysis of the data.

In embodiments, the IMD 102 and/or the EMD 106 may be configured to provide therapy. Therapy may be provided automatically and/or upon request (e.g., an input by the subject 104, a clinician, another device or process, and/or the like). The IMD 102 and/or the EMD 106 may be programmable in that various characteristics of their sensing, therapy (e.g., duration and interval), and/or communication may be altered by communication between the devices 102 and 106 and/or other components of the system 100.

According to embodiments, the IMD 102 may include any type of IMD, any number of different components of an implantable system, and/or the like. For example, the IMD 102 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the subject 104 and/or the IMD 102. In various embodiments, the IMD 102 may include both defibrillation and pacing/CRT capabilities (e.g., a CRT-D device).

In embodiments, the IMD 102 may be implanted subcutaneously within an implantation location or pocket in the patient's chest or abdomen and may be configured to monitor (e.g., sense and/or record) physiological parameters associated with the patient's heart. In embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac electrical signals, heart sounds, heart rate, blood pressure measurements, oxygen saturations, and/or the like.

In embodiments, the IMD 102 may be configured to detect a variety of physiological signals that may be used in connection with various diagnostic, therapeutic and/or monitoring implementations. For example, the IMD 102 may include sensors or circuitry for detecting respiratory system signals, cardiac system signals, heart sounds. and/or signals related to patient activity. In embodiments, the IMD 102 may be configured to sense intrathoracic impedance, from which various respiratory parameters may be derived, including, for example, respiratory tidal volume and minute ventilation.

In embodiments, sensors and associated circuitry may be incorporated in the IMD 102 for detecting one or more body movement or body posture and/or position related signals. For example, accelerometers and/or GPS devices may be employed to detect patient activity, patient location, body orientation, and/or torso position. According to embodiments, for example, the MD 102 may include an acceleration sensor 110 configured to generate an acceleration signal and/or acceleration data, which may include the acceleration signal, information derived from the acceleration signal, and/or the like. In embodiments, the acceleration data includes acceleration measurements associated with movement of the MD 102. In embodiments, the acceleration sensor may be, or include, any acceleration sensor able to generate measurements associated with its motion. An "acceleration sensor," as used herein, may be, or include, any type of accelerometer, gyroscope, magnetometer, inertial measurement unit (IMU), and/or any other type of sensor or combination of sensors configured to measure changes in acceleration, angular velocity, and/or the like. According to embodiments, acceleration data may be used to determine that the IMD 102 has flipped.

Derived parameters may also be monitored using the IMD 102. For example, a sleep sensor may rely on measurements taken by an implanted accelerometer that measures body activity levels. The sleep sensor may estimate sleeping patterns based on the measured activity levels. Other derived parameters include, but are not limited to, a functional capacity indicator, autonomic tone indicator, sleep quality indicator, cough indicator, anxiety indicator, and a cardiovascular wellness indicator for calculating a quality of life indicator quantifying a subject's overall health and well-being.

In various embodiments, the EMD 106 may be a device that is configured to be portable with the subject 104, e.g., by being integrated into a vest, belt, harness, sticker; placed into a pocket, a purse, or a backpack; carried in the subject's hand; and/or the like, or otherwise operatively (and/or physically) coupled to the subject 104. The EMD 106 may be configured to monitor (e.g., sense and/or record) physiological parameters associated with the subject 104 and/or provide therapy to the subject 104. For example, the EMD 106 may be, or include, a wearable cardiac defibrillator (WCD) such as a vest that includes one or more defibrillation electrodes. In embodiments, the EMD 106 may include any number of different therapy components such as, for example, a defibrillation component, a drug delivery component, a neurostimulation component, a neuromodulation component, a temperature regulation component, and/or the like. In embodiments, the EMD 106 may include limited functionality, e.g., defibrillation shock delivery and communication capabilities, with arrhythmia detection, classification and/or therapy command/control being performed by a separate device such as, for example, the IMD 102.

In embodiments, the EMD 106 may include sensing components such as, for example, one or more surface electrodes configured to obtain an electrocardiogram (ECG), one or more accelerometers configured to detect motion associated with the patient 104, one or more respiratory sensors configured to obtain respiration information, one or more environmental sensors configured to obtain information about the external environment (e.g., temperature, air quality, humidity, carbon monoxide level, oxygen level, barometric pressure, light intensity, sound, and/or the like) surrounding the patient 104, and/or the like. In embodiments, the EMD 106 may be configured to measure parameters relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like.

According to embodiments, the EMD 106 may be configured to measure subjective and/or perceptive data from the subject 104. Subjective data is information related to a patient's feelings, perceptions, and/or opinions, as opposed, for example, to objective physiological data. For example, EMD 106 may be configured to measure subject responses to inquiries such as "How do you feel?" and "How is your pain?" The EMD 106 may be configured to prompt the subject 104 and record subjective data from the subject 104 using visual and/or audible cues. In embodiments, the subject 104 can press coded response buttons or type an appropriate response on a keypad. In embodiments, subjective data may be collected by allowing the subject 104 to speak into a microphone and using speech recognition software to process the subjective data.

The illustrative cardiac monitoring system 100 shown in FIG. 1 is not intended to suggest any limitation as to the scope of use or functionality of embodiments of the present disclosure. The illustrative cardiac monitoring system 100 should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein.

Various components depicted in FIG. 1 may operate together to form the monitoring system 100, which may be, for example, a computerized patient management and monitoring system. In embodiments, the system 100 may be designed to assist in monitoring the subject's condition, managing the subject's therapy, and/or the like. An illustrative patient management and monitoring system is the LATITUDE® patient management system from Boston Scientific Corporation, Natick Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

Figure 2:
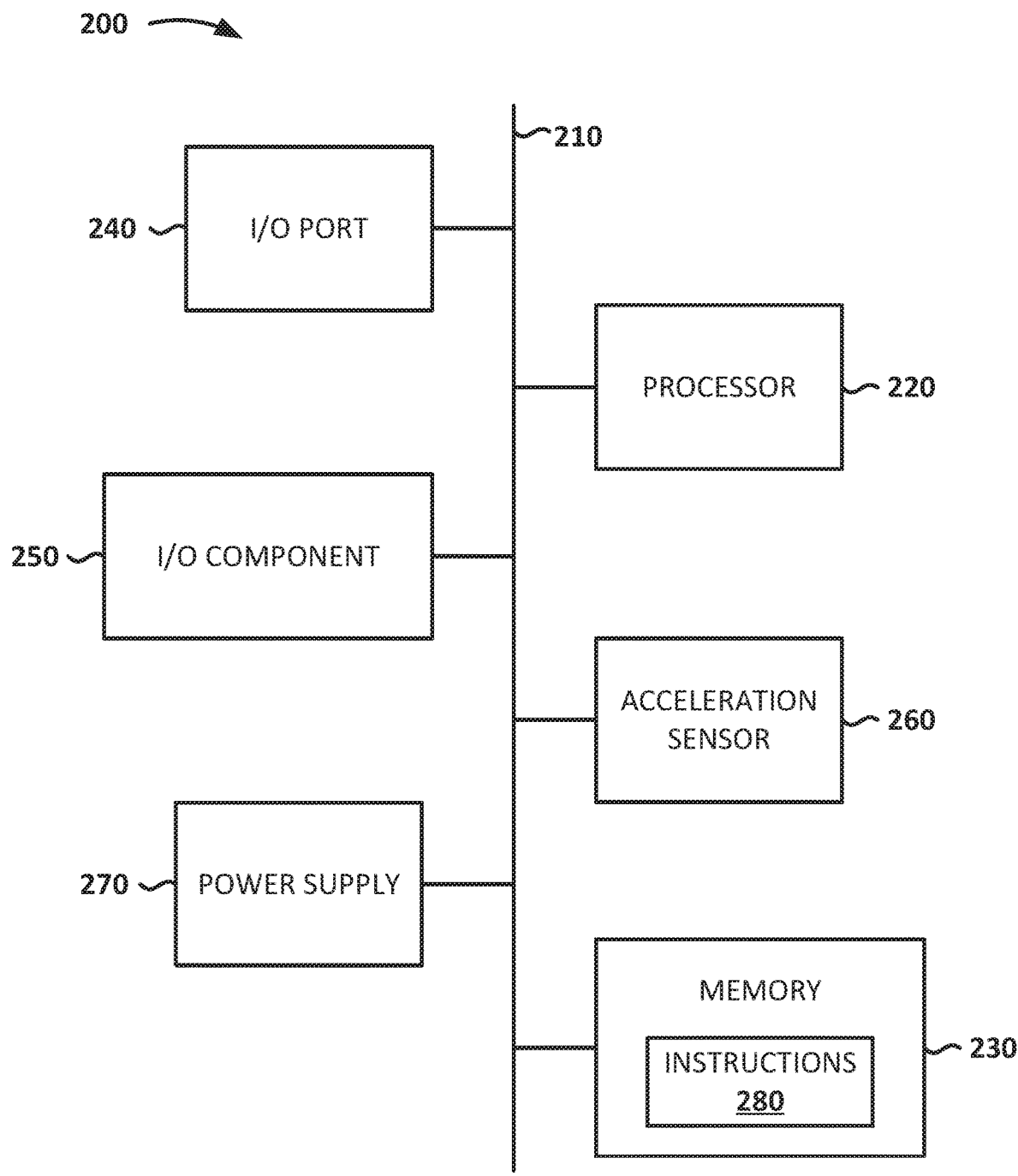
FIG. 2 is a block diagram depicting an illustrative computing device, in accordance with embodiments of the disclosure.

Any number of components of the system 100 may be implemented using one or more computing devices. That is, for example, IMD 102 and/or EMD 106 may be implemented on one or more computing devices. FIG. 2 is a block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "hand-held devices," "smartphones," "general-purpose graphics processing units (GPGPUs)," and the like, all of which are contemplated within the scope of FIGS. 1 and 2, with reference to various components of the system 100 and/or computing device 200.

In embodiments, the computing device 200 includes a bus 210 that, directly and/or indirectly, couples the following devices: a processor 220, a memory 230, an input/output (I/O) port 240, an I/O component 250, an acceleration sensor 260 (e.g., the acceleration sensor 110 depicted in FIG. 1), and a power supply 270. Any number of additional components, different components, and/or combinations of components may also be included in the computing device 200. The I/O component 250 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like. The acceleration sensor 260 may be any type of sensor capable of measuring acceleration such as, for example, an accelerometer, an inertial measurement unit (IMU), a magnetometer, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, a number of acceleration sensors 260, and/or a number of power supplies 270. Additionally, any number of these components, or combinations thereof, may be distributed and/or duplicated across a number of computing devices.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 280 for causing the processor 220 to implement aspects of embodiments of system components discussed herein and/or to perform aspects of embodiments of methods and procedures discussed herein.

The computer-executable instructions 280 may include, for example, computer code, machine-useable instructions, and the like such as, for example, program components capable of being executed by one or more processors 220 associated with the computing device 200. Program components may be programmed using any number of different programming environments, including various languages, development kits, frameworks, and/or the like. Some or all of the functionality contemplated herein may also, or alternatively, be implemented in hardware and/or firmware.

Figure 3:
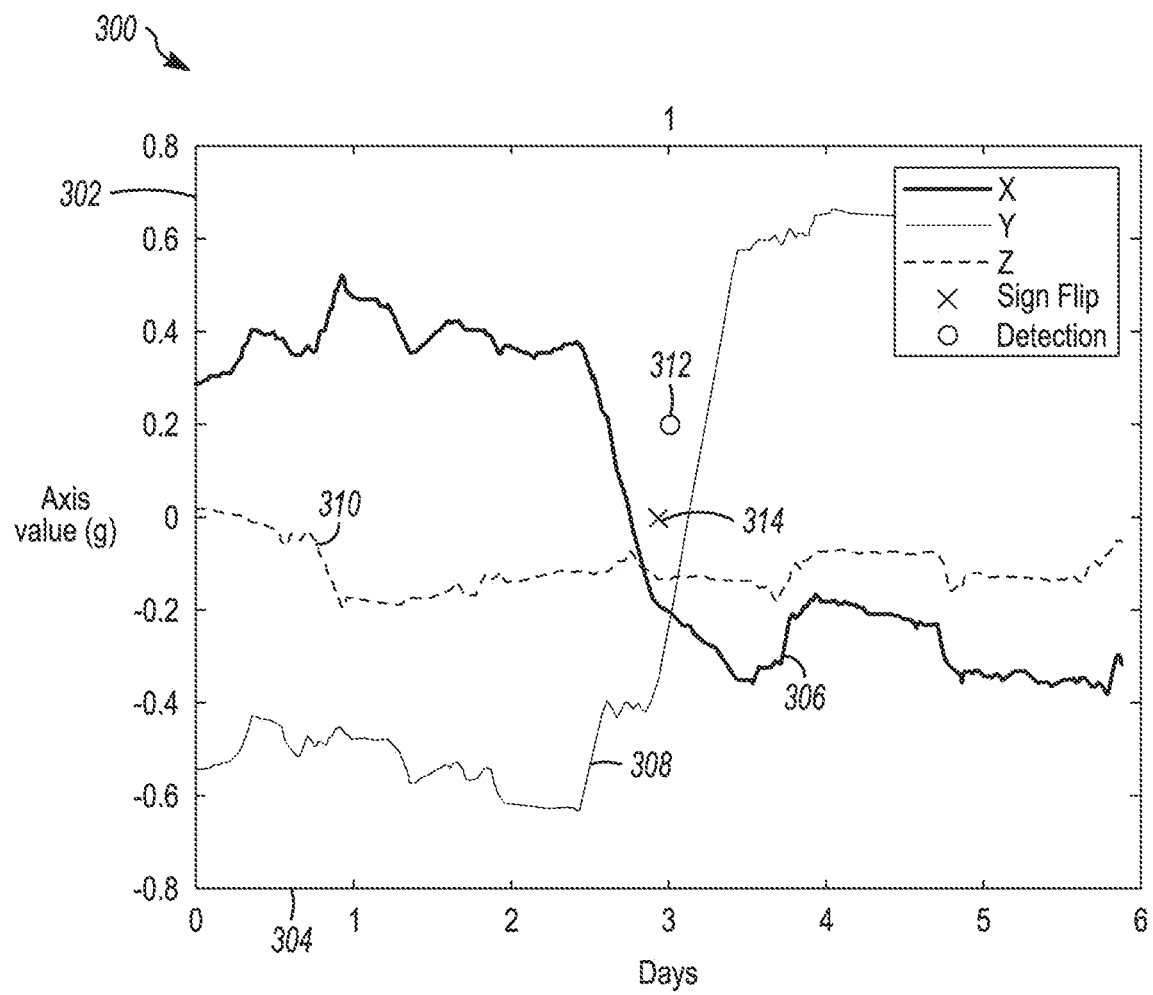
FIG. 3 depicts an illustrative plot of acceleration data axis values, in accordance with embodiments of the disclosure.

According to embodiments, for example, the instructions 280 may be configured to be executed by the processor 220 and, upon execution, to cause the processor to obtain acceleration data from the acceleration sensor 260 and to determine, based on the acceleration data, whether the IMD has flipped. According to embodiments, the instructions 280 may be configured to cause the processor 220 to determine that the medical device has flipped by causing the processor to generate a slope of the acceleration data. An example of an illustrative plot 300 including generated slopes, in accordance with embodiments of the subject matter disclosed herein, is depicted in FIG. 3.

As shown, the plot 300 includes axis values for at least one axis plotted against time. In the example illustrated, the plot 300 includes a vertical chart axis 302 corresponding to acceleration sensor axis values and a horizontal chart axis 304 corresponding to time (in days). A first set 306 of axis values corresponding to an X axis is plotted against time, a second set 308 of axis values corresponding to a Y axis is plotted against time, and a third set 310 of axis values corresponding to a Z axis is plotted against time.

According to embodiments, the illustrated sets of axis values 306, 308, and 310 may be smoothed sets of axis data. That is, for example, in embodiments, the instructions 280 may be configured to cause the processor 220 to apply a moving mean filter across the data to generate at least a first smoothed set of axis data corresponding to a first axis, a second smoothed set of axis data corresponding to a second axis, and/or a third smoothed set of axis data corresponding to a third axis. As shown, the processor 220 may be configured to identify an intersection, at the point in time marked by the circle 312 in FIG. 3, of the first smoothed set 306 of axis values and the second smoothed set 308 of axis values. The processor 220 may determine, based on the identified intersection, that the medical device has flipped.

Additionally, or alternatively, the processor 220 may identify a flip about a particular axis (e.g., the x-axis, y-axis, or z-axis) using one or more trigonometric functions. For example, to identify a flip about an x-axis, the processor 200 may compute an angle using the y-axis value and z-axis value illustrated in FIG. 3 using, for example, a 4-quadrant arctangent function, i.e., $\theta = a\tan 2d(y,z)$. If the IMD 102 does not flip, then this angle should be relatively constant. If, however, the IMD 102 flips, then this angle should change by about 180°. In embodiments, the processor 220 may identify a flip if the angle changes by more than a threshold amount (e.g., greater than 90°, 110°, 130°, 150°, 170°, and/or the like). Similarly, the processor 220 may identify a flip about the y-axis when the angle of $\theta = a\tan 2d(x,z)$ changes by more than a threshold amount (e.g., greater than 90°, 110°, 130°, 150°, 170°, and/or the like). And, the processor 220 may identify a flip about the z-axis when the angle of $\theta = a\tan 2d(x,y)$ changes by more than a threshold amount (e.g., greater than 90°, 110°, 130°, 150°, 170°, and/or the like). In at least some embodiments, other trigonometric functions that are used to calculate angles between the x-axis value and the y-axis value, between the x-axis value and the z-axis value, and the y-axis value and the z-axis value.

As another example of using a trigonometric function to identify a flip, the processor 220 may compute the angle between any two vectors in a three-dimensional space. For example, the processor 220 may compute the angle between the smoothed vector $v_1=(x_1, y_1, z_1)$ at a first time point and the smoothed vector $v_2=(x_2, y_2, z_2)$ at a second time point using, for example, $\theta = \cos^{-1}(v_1 \cdot v_2)/(|v_1|v v_2|)$. Here, $x_i$, $y_i$, $z_i$ are the axis values at time points and $v_1 \cdot v_2$ is the dot product of $v_1$ and $v_2$, i.e. $v_1 \cdot v_2 = x_1 x_2 + y_1 y_2 + z_1 z_2$, and $|v_i| = \text{sqrt}(x_i^2 + y_i^2 + z_i^2)$. In embodiments, the first time point may occur prior to the second time point so the processor 220 can identify how the vector changes over time. For example, if no flip occurs, the angle between the vectors at the two time points will be approximately zero. If, however, a flip occurs, the angle between the vectors at the two time points will be approximately 180°. In embodiments, the processor 220 may identify a flip if the angle is more than a threshold amount (e.g., greater than 90°, 110°, 130°, 150°, 170°, and/or the like).

In at least some embodiments, however, the processor 220 may not compute $\cos^{-1}$ of $(v_1 \cdot v_2)/(|v_1||v_2|)$ and instead, the processor 220 may identify a flip based on $(v_1 \cdot v_2)/(|v_1|vv_2|)$. For example, if $\cos^{-1}(v_1 \cdot v_2)/(|v_1||v_2|)$ is approximately zero, then $(v_1 \cdot v_2)/(|v_1||v_2|)$ will be approximately +1. Conversely, if $\cos^{-1}(v_1 \cdot v_2)/(|v_1||v_2|)$ is approximately 180°, then $(v_1 \cdot v_2)/(|v_1||v_2|)$ will be approximately −1. As such, instead of computing $\cos^{-1}(v_1 \cdot v_2)/(|v_1||v_2|)$, the processor 220 may compute $(v_1 \cdot v_2)/(|v_1||v_2|)$ and determine when $(v_1 \cdot v_2)/(|v_1|vv_2|)$ exceeds a specific threshold (e.g., 0 is equivalent to 90°, −0.707 is equivalent to 135°, etc.) to identify a flip of the IMD 102. In at least some other embodiments, when the patient is at rest, the processor may compute $(v_1 \cdot v_2)$ instead of computing $(v_1 \cdot v_2)/(|v_1||v_2|)$ to determine a flip because $(|v_1||v_2|)$ would be approximately 1(G).

Alternatively, or additionally, the processor 220 may identify a first sign change associated with the first smoothed set 306 of axis data, a second sign change associated with the second smoothed set 308 of axis data, and/or a third sign change associated with the third smoothed set 310. That is, the processor 220 identifies a point in time 314 at which the axis values of the first set, the second set, and/or the third set becomes negative. In embodiments, the instructions 280 may be configured to cause the processor to determine, based on the identified first sign change, the second sign change, and/or the third sign change, that the medical device has flipped. According to embodiments, in response to determining that the IMD 102 has flipped, the processor 220 may be further configured to generate a notification to clinicians and/or to the patient that the IMD 102 may have moved within the pocket and suggest that the clinicians and/or the patient perform a body calibration procedure to account for the new orientation.

According to embodiments, in response to determining that the medical device has flipped, the instructions 280 may be further configured to cause the processor 220 to apply correction to an output of a monitoring process. In embodiments, for example, the monitoring process may include a posture algorithm, a heart sounds algorithm, a medical device impedance sensing process, and/or the like. According to embodiments, the instructions 280 may be configured to cause the processor 220 to apply the correction to the output of the monitoring process by recalibrating the monitoring process to account for a flipped orientation of the medical device. In embodiments, the processor 220 may be configured to send a notification to a clinician and/or the patient about the flip and may include one or more recommendations for responding to the flip.

The illustrative computing device 200 shown in FIG. 2 and plot 300 shown in FIG. 3 are not intended to suggest any limitation as to the scope of use or functionality of embodiments of the present disclosure. The illustrative computing device 200 and plot 300 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 4A:
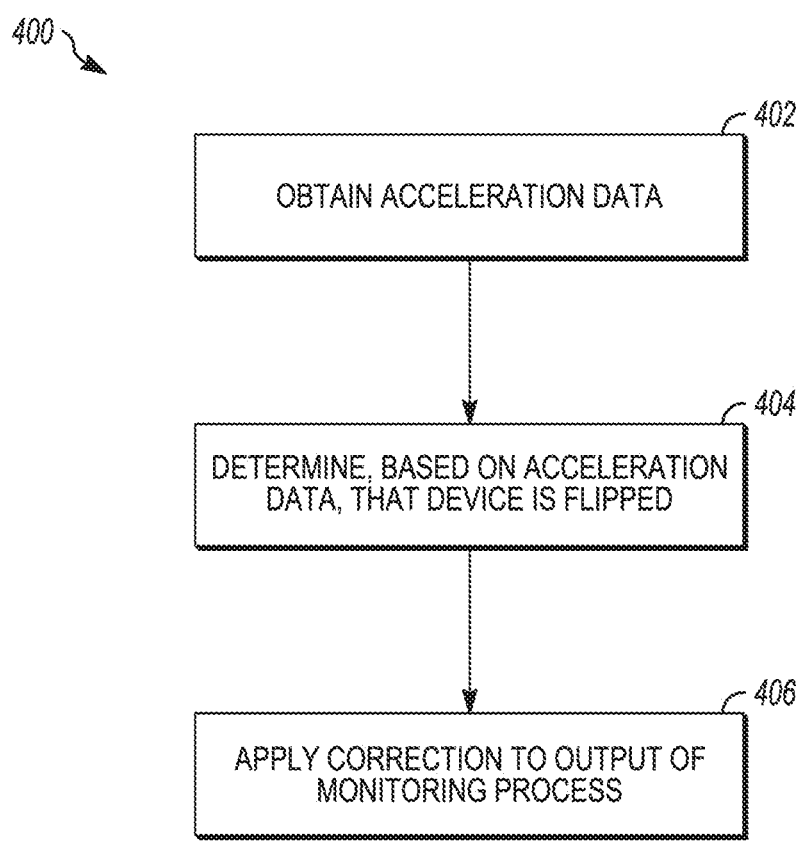
FIG. 4A is a flow diagram depicting an illustrative method of medical device operation, in accordance with embodiments of the disclosure.

FIG. 4A is a flow diagram depicting an illustrative method 400 of medical device operation (e.g., physiological monitoring), in accordance with embodiments of the subject matter disclosed herein. According to embodiments, the method 400 may be performed by any number of different aspects of components of the system 100 depicted in FIG. 1, and/or the computing device 200 depicted in FIG. 2. For example, in embodiments, the illustrative method 400 may be performed by a mobile device having an acceleration sensor (e.g., an accelerometer and/or a magnetometer), a processor, and a memory, as described herein.

Embodiments of the method 400 include obtaining acceleration data from an acceleration sensor (block 402) and determining, based on the acceleration data, that the medical device has flipped (block 404). According to embodiments, the acceleration data may include, for example, posture data captured by an acceleration sensor such as an accelerometer, inertial measurement unit (IMU), magnetometer, and/or the like. In embodiments, analyzing the acceleration data over time may reveal device orientation changes. That is, for example, in embodiments, obtaining the acceleration data may include sampling an output of an acceleration sensor at a specified time interval. For example, the acceleration data may include sampling an output of an acceleration sensor many times a second, once every second, once every minute, two minutes, three minutes, four minutes, five minutes, six minutes, seven minutes, eight minutes, nine minutes, ten minutes, eleven minutes, etc.

As shown in FIG. 4A, the method 400 may further include applying a correction to an output of a monitoring process (block 406). According to embodiments, the orientation of a sensor in a medical device (and thus, the orientation of the medical device itself) may be an assumption or input to any number of decision processes, monitoring process, therapy processes, and/or the like. For example, a posture determining algorithm may depend upon a fixed orientation. That is for example, a sleep incline algorithm may be disrupted if the medical device flips. Similarly, a heart sounds algorithm may depend upon a fixed device orientation. In embodiments, for example, a heart sounds algorithm may be configured to detect the waveform of S2 and use its peak as a fiducial marker. Flipping the medical device would invert the waveform and the heart sounds algorithm may select a less accurate range of data for S3 measurements, which will reduce heart logic accuracy. A device impedance sensing process also may depend upon a fixed device orientation. That is, for example, if the medical device is flipped, the impedance vector will change, thereby causing the amplitude of the signal to jump, which may result in impaired impedance sensing.

Accordingly, in embodiments, any number of different monitoring processes may be corrected to account for the fact that the device orientation has changed from its assumed (or previously determined) orientation. Applying a correction to an output of a monitoring process may be achieved by modifying an output directly and/or by recalibrating the monitoring process to account for the different (e.g., flipped) orientation of the medical device. In embodiments, the monitoring process may include, for example, a posture algorithm (e.g., an algorithm configured to monitor a sleep incline), a heart sounds algorithm, and/or a medical device impedance sensing process.

Figure 4B:
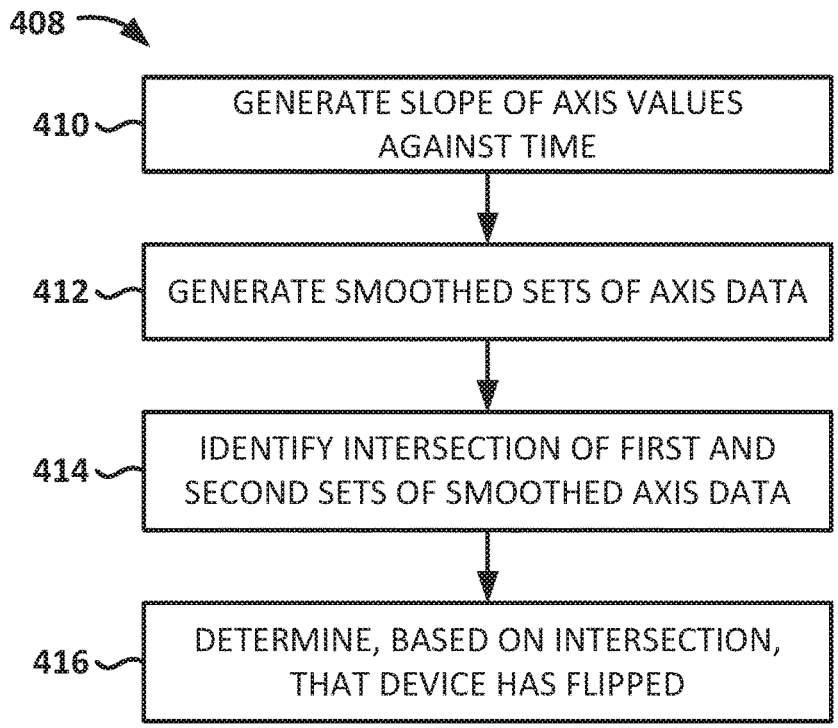
FIG. 4B is a flow diagram depicting an illustrative method of determining that a medical device has flipped, in accordance with embodiments of the disclosure.

FIG. 4B is a flow diagram depicting an illustrative method 408 of determining that a medical device has flipped, in accordance with embodiments of the subject matter disclosed herein. According to embodiments, the method 400 may be performed by any number of different aspects of components of the system 100 depicted in FIG. 1, and/or the computing device 200 depicted in FIG. 2. For example, in embodiments, the illustrative method 400 may be performed by a mobile device having an acceleration sensor (e.g., an accelerometer and/or a magnetometer), a processor, and a memory, as described herein.

As shown in FIG. 4B, the method 408 may include generating a slope of the acceleration data (block 410), the plot comprising axis values for at least two axes plotted against time; applying a moving mean filter across the data to generate a first smoothed set of axis data corresponding to a first axis and a second smoothed set of axis data corresponding to a second axis (block 412); identifying an intersection of the first smoothed set of axis data and the second smoothed set of axis data (block 414); and determining, based on the identified intersection, that the medical device has flipped (block 416).

Figure 4C:
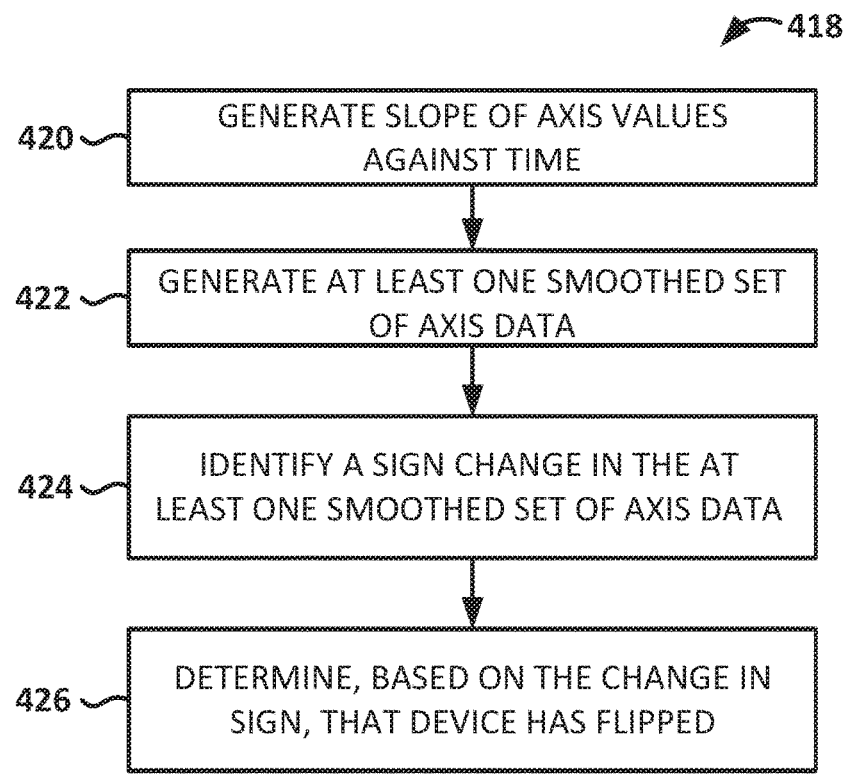
FIG. 4C is a flow diagram depicting another illustrative method of determining that a medical device has flipped, in accordance with embodiments of the disclosure.

FIG. 4C is another flow diagram depicting another illustrative method 418 of determining that a medical device has flipped, in accordance with embodiments of the subject matter disclosed herein. The method 418 may be utilized in lieu of, or in addition to, the method 408 depicted in FIG. 4B. According to embodiments, the method 418 may be performed by any number of different aspects of components of the system 100 depicted in FIG. 1, and/or the computing device 200 depicted in FIG. 2. For example, in embodiments, the illustrative method 400 may be performed by a mobile device having an acceleration sensor (e.g., an accelerometer and/or a magnetometer), a processor, and a memory, as described herein.

As shown in FIG. 4C, the method 418 may include generating a slope of the acceleration data, the slope comprising axis values for at least one axis against time (block 420); applying a moving mean filter across the data to generate a first smoothed set of axis data corresponding to a first axis, a second smoothed set of axis data corresponding to a second axis, and/or a third smoothed set of axis data corresponding to a third axis (block 422); identifying a first sign change associated with the first smoothed set of axis data, identifying a second sign change associated with the second smoothed set of axis data, and/or identifying a third sign change associated with third smoothed set of axis data (block 424); and determining, based on the identified first sign change, the second sign change, and/or the third sign change, that the medical device has flipped (block 426). In embodiments, block 424 may additionally, or alternatively include using a trigonometric function on the axes data, as described above in relation to FIG. 3.

Various modifications and additions can be made to the exemplary embodiments discussed without departing from the scope of the disclosed subject matter. For example, while the embodiments described above refer to particular features, the scope of this disclosure also includes embodiments having different combinations of features and embodiments that do not include all of the described features. That is, for example, embodiments may include one or more filters and/or other components that facilitate interpreting sensed physiological signals in the presence of some interference caused by having an energy supply current sharing a portion of the physical sense pathway. Accordingly, the scope of the disclosed subject matter is intended to embrace all such alternatives, modifications, and variations as fall within the scope of the claims, together with all equivalents thereof.

We claim:

1. A medical device comprising:
a processor;
an acceleration sensor configured to generate acceleration data, the acceleration data comprising a plurality of acceleration measurements; and
a memory having embodied thereon computer-executable instructions that are configured to, when executed by the processor, cause the processor to:
 obtain the acceleration data from the acceleration sensor;
 determine, based on the acceleration data, that the medical device has changed its orientation with respect to at least one axis by more than 110 degrees; and
 apply a correction to a heart sounds algorithm by recalibrating the heart sounds algorithm to account for a flipped orientation of the medical device, wherein the correction is applied in response to determining that the medical device has changed its orientation with respect to the at least one axis by more than 110 degrees.

2. The medical device of claim 1, wherein the instructions are further configured to cause the processor to generate a notification, in response to determining that the medical device has changed its orientation with respect to the at least one axis by more than 110 degrees.

3. The medical device of claim 2, wherein the notification comprises one or more recommendations for responding to the changed orientation.

4. The medical device of claim 1, wherein the instructions are configured to cause the processor to determine that the medical device has changed its orientation with respect to the at least one axis by more than 110 degrees by causing the processor to:
 apply a trigonometric function to the acceleration data and identify the changed orientation based on a resultant of the trigonometric function being applied to the acceleration data.

5. The medical device of claim 4, wherein the trigonometric function comprises a 4-quadrant arctangent function.

6. A processor-implemented method, performed by a processor of a medical device, the method comprising:
 obtaining acceleration data from an acceleration sensor of the medical device;
 generating a first smoothed set of axis data corresponding to a first axis and a second smoothed set of axis data corresponding to a second axis by applying a moving mean filter to the acceleration data;
 determining that the medical device has flipped based on the first smoothed set of axis data; and
 applying, in response to determining that the medical device has flipped, a correction to an output of a heart sounds algorithm.

7. The method of claim 6, wherein the determining that the medical device has flipped comprises:
 identifying an intersection between the first smoothed set of axis data and the second smoothed set of axis data; and
 determining, based on the identified intersection, that the medical device has flipped.

8. The method of claim 6, wherein the determining that the medical device has flipped comprises:
 identifying a first sign change associated with the first smoothed set of axis data; and
 determining, based on the identified first sign change, that the medical device has flipped.

9. The method of claim 8, further comprising: identifying a second sign change associated with the second smoothed set of axis data; and determining, based on the identified first and second sign changes, that the medical device has flipped.

10. One or more non-transitory computer-readable media having computer-executable instructions embodied thereon, the instructions configured to be executed by a processor, wherein the instructions are configured to cause the processor to:
 determine, based on acceleration data, that a medical device has flipped 180 degrees; and
 apply, in response to determining that the medical device has flipped, a correction to a heart sounds algorithm.

11. The media of claim 10, wherein the instructions are configured to cause the processor to determine that the medical device has flipped by causing the processor to:
 apply a moving mean filter across the acceleration data to generate a first smoothed set of axis data corresponding to a first axis and a second smoothed set of axis data corresponding to a second axis;
 identify an intersection between the first smoothed set of axis data and the second smoothed set of axis data; and
 determine, based on the identified intersection, that the medical device has flipped.

12. The media of claim 10, wherein the instructions are configured to cause the processor to determine that the medical device has flipped by causing the processor to:
 apply a moving mean filter across the acceleration data to generate a first smoothed set of axis data corresponding to a first axis of the at least one axis;
 identify a first sign change associated with the first smoothed set of axis data; and
 determine, based on the identified first sign change, that the medical device has flipped.

13. The media of claim 10, wherein the heart sounds algorithm is configured to detect a waveform of S2.

14. The media of claim 10, wherein the instructions are configured to cause the processor to determine that the medical device has flipped by causing the processor to:
 apply a trigonometric function to the acceleration data and identify a flip based on a resultant of the trigonometric function being applied to the acceleration data.

15. The media of claim 14, wherein the trigonometric function comprises a 4-quadrant arctangent function.

16. The media of claim 14, wherein the trigonometric function comprises computing and comparing an angle between two vectors in a three-dimensional space.

* * * * *